United States Patent [19]
Gernandt et al.

[11] 4,080,593
[45] Mar. 21, 1978

[54] APPARATUS FOR THE DETECTION OF LIQUID COMPONENTS IN GASES FOR DRY-RUNNING COMPRESSORS

[75] Inventors: Helmut Gernandt, Cologne-Poll; Heinz Heeg, Wesseling, both of Germany

[73] Assignee: Linde Aktiengesellschaft, Wiesbaden, Germany

[21] Appl. No.: 730,724

[22] Filed: Oct. 8, 1976

[30] Foreign Application Priority Data
Oct. 9, 1975 Germany .......................... 2545354

[51] Int. Cl.² ............................................. G08B 21/00
[52] U.S. Cl. ................................... 340/235; 340/242
[58] Field of Search ............................. 340/235, 242

[56] References Cited
U.S. PATENT DOCUMENTS

| | | |
|---|---|---|
| 3,350,941 | 11/1967 | Misevich et al. .................. 340/235 |
| 3,460,123 | 8/1969 | Bass ..................................... 340/235 |
| 3,530,855 | 9/1970 | Balding ........................... 340/235 X |
| 3,940,754 | 2/1976 | Weber ................................. 340/242 |

Primary Examiner—John W. Caldwell, Sr.
Assistant Examiner—Daniel Myer
Attorney, Agent, or Firm—Karl F. Ross

[57] ABSTRACT

A device for the detection of liquid components in gases, especially to detect the presence of liquids such as lubricants in gases subjected to compression in dry-running compressors, comprises an electric capacitor having a moisture-receptive dielectric with dielectric constant varying from a normal dielectric constant in the presence of the absorbed liquid. The capacitor is connected in a capacitance-detection circuit and can operate an alarm or the like.

5 Claims, 5 Drawing Figures

APPARATUS FOR THE DETECTION OF LIQUID COMPONENTS IN GASES FOR DRY-RUNNING COMPRESSORS

FIELD OF THE INVENTION

The present invention relates to the detection of liquid components in gases and, more particularly, to improvements in the operation of dry-running compressors which are adversely affected by liquid (lubricant) droplets or entrainment or even small quantities of liquid with the compressed gas.

BACKGROUND OF THE INVENTION

Dry-running compressors are generally piston-type machine in which the gas-compression chamber must be kept free from particles of the liquid lubricants normally used upon the other parts of the machine to prevent wear or to provide an effective seal. A typical application for such dry-running compressors is the compression of oxygen in which the presence of liquid components, especially oil, is highly disadvantageous and unsafe for most uses.

For an effective separation of the lubricant-coated parts from the compression chamber of such dry-running compressor, it is customary to provide oil-stripping rings or the like as part of the seals separating the lubricant-containing chambers from the chamber exposed to the gas to be compressed. Such oil-stripping rings can remove the oil film mechanically from the piston rod, for example, and prevent practically any incursion of the oil into the space to be later occupied by the gas or traversed by those piston parts which come into contact with the gas.

It is therefore important that the gases processed in a dry-running compressor be free from liquids and especially from the lubricating oil of the dry-running compressor. On the other hand, the presence of oils or, in general terms, liquid in the gas is indicative of a failure of the oil-stripping system and the sealing devices which prevent incursion of the oil into the gas spaces. In the past the techniques for preventing oil from bypassing the stripping ring and entering the gas space has been to periodically disassemble the apparatus and replace the parts when signs or air were noted, or to await the development of noticeable amounts of oil in the gas, using this as a sign that replacement of the oil-stripping rings and seals was necessary.

The disadvantages of such systems will be apparent since, in the first case, the apparatus was forced into a maintenance program unnecessarily prematurely in some cases while, with the other system, contamination of the gases and of the dry-running parts was necessary before corrective action could be taken.

It has been desirable to provide a substantially automatic system for the detection of liquid components in the gases of a dry-running machine of the aforedescribed type to permit operation thereof under optimum conditions.

OBJECTS OF THE INVENTION

It is an object of the present invention to provide a detection system for liquid components in a gas which is especially adapted to dry-running compressors and can afford automatic detection of the failure of the oiling-stripping and sealing parts thereof.

Still another object of the invention is to provide, in a dry-running machine, a system for monitoring the effectiveness of the oil-stripping components at locations remote from the machine.

Still another object of the invention is to provide an improved device for detecting the presence of liquid components in gases in an automatic and remotely monitorable manner.

SUMMARY OF THE INVENTION

These objects and others which will become apparent hereinafter are attained, in accordance with the present invention, with the use of an electrical capacitor as a liquid detector, the capacitance having a liquid-receptive dielectric whose dielectric constant varies as a function of the absorption of liquid.

It should be understood that the terms "liquid" and "moisture" are not limited to oils or other lubricants although droplets moisture of oils and lubricants are the most common liquid components of the gases of dry-running compressors. Thus whenever a moisture-receptive dielectric is described herein it will be understood to include dielectrics capable of taking up oil droplets, oil mists, lubricant particles of all types and other liquid which may be entrained by the gas which is to be monitored.

According to an important feature of the invention, the electrical capacitor is disposed in the space traversed or containing the gas to be monitored and advantageously the dielectric is exposed to the gas in this space, preferably through openings in one of the plates of the capacitor. In the case in which oil sprays from an oil stripper, for example, represent a failure of this component, the capacitor may be provided proximal to the oil stripper or in the path of such sprayed particles so that an early warning of failure may be obtained.

With variation of the dielectric constant of the liquid-receptive dielectric, there is a change in the electrical capacity of the capacitor or condenser and this change may be applied to an electrical capacitance-sensitive circuit, e.g. a resonance network or capacitor bridge, to operate an alarm or warning circuit.

Most advantageously, the circuit comprises a reference capacitor whose preset capacitance is equal to the normal capacitance of the detecting capacitor so that a balance between the two indicates a normal state of operation of the machine and the absence of liquid components in the aforementioned gas space. In the presence of particles of liquid, however, the dielectric constant of the liquid-receptive dielectric of the detected capacitor changes, the capacitance of this component changes and the difference between the capacitance of the detector and the capacitance of the reference condenser results in a signal in the circuit which can be used to operate a remote detector, to trigger an alarm or to perform some other essential operation directly or to induce a human operator to perform such an action. For example the circuit may automatically cut off operation of the dry-running compressor.

While reference has been made here to a liquid-receptive dielectric and we prefer to use a solid and especially a bibulous material such as felted or matted paper (e.g. filter paper), nonwoven fabric webs and other cellulosic fibrous materials have a highly absorptivity for droplets of liquids such as oil, practically any other dielectric whose dielectric constant will change in the presence of the liquid may be used. For example, the dielectric may be air or even the gas which is to be monitored for the presence of moisture.

The device of the present invention has been found to be particularly advantageous for use in dry-running compressors for the compression of oxygen on grounds of safety and reliability. In general it has been found to be successful for dry-running compressors for fluids in which high purity must be maintained and which must be kept free from all kinds of liquids including water, oils or the like. Nevertheless it has been found to be practical for the detection of the presence of moisture and liquid droplets in other gases such as air.

According to a feature of the invention, the electric detector capacitor of the present invention is a plate-type condenser, i.e. a condenser consisting of two conductive plates with the dielectric disposed between them. Advantageously, the plate condenser is annular, i.e. formed as a ring, and is particularly adapted to be disposed about the piston rod of a dry-running compressor or a shaft traversing an oil seal. So that the plate of the condenser has to be spaced apart by considerable distances to provide an effective capacitance and to enable the gases of the space to be monitored to reach the dielectric, the capacitor can comprise a copper plate, a liquid-receptive dielectric and, as the other plate, a copper mesh of fabric composed of interwoven copper wires. The dielectric is preferably blotting paper.

The oil detector is disposed preferably in the regions of a dry-running compressor oil-stripping ring and the stop bushings thereof so that the copper plates of the capacitances can be mounted against the stop bushing and the oil-stripping ring, respectively. Especially when the dry-running compressor is used for the compression of oxygen, the circuit may be provided with an alarm which is triggered by a change in the dielectric constant of the capacitor dielectric. Several problems with the dry-running compressor can be avoided when the alarm device includes a signal which is automatically terminated with a change in the dielectric constant.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
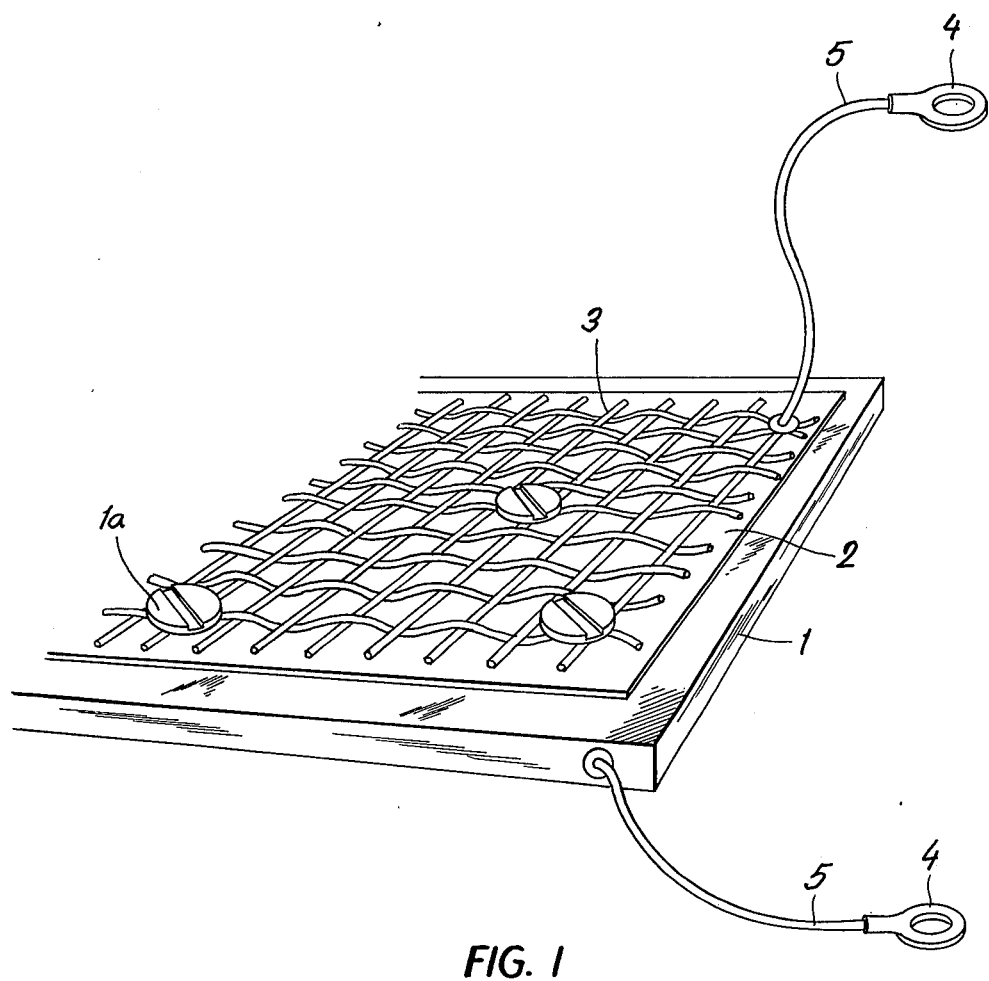
FIG. 1 is a fragmentary perspective view, somewhat in diagrammatic form, of a detector according to the present invention.

FIG. 1 of the drawing shows a liquid-detection capacitor for use in a gas environment and specifically for the detection of liquid, especially lubricating oil entrained by a gas subjected to a dry-running compressor.

The detector comprises a plate-type capacitor having, as a base plate, a copper slab 1 of rectangular outline, a blotting paper dielectric 2 and a fluid-permeable conductive plate 3 formed as a rectangular copper fabric substantially coextensive with the rectangular blotting paper sheet 2. The copper fabric 3 can be woven from copper wire and is secured to the copper slab 1 by plastic screws 1a. The plates, of course, can be composed of other conductive materials. Instead of a fabric plate, the permeable member can be a perforated or slit plate. Of course, when a substantial spacing can be provided between the plates it is not necessary to use a permeable plate at all as long as a clearance for the penetration of the liquid entrained by the gas to the dielectric is possible.

Conductors 5 provided with terminals 4 are soldered to the plate 1 and the wire mesh 3 and facilitate connection of the detector to the circuit. As will be apparent from the foregoing, the capacitor, in the absence of liquid components of the ambient gas has a characteristic dielectric constant and capacitor. In the presence of liquid components which are readily picked up by the bibulous dielectric, the dielectric constant is altered and the capacitance changed. The detecting circuit can be a capacitance bridge or an oscillating circuit in which the capacitor controls the frequency or phase.

Figure 2:
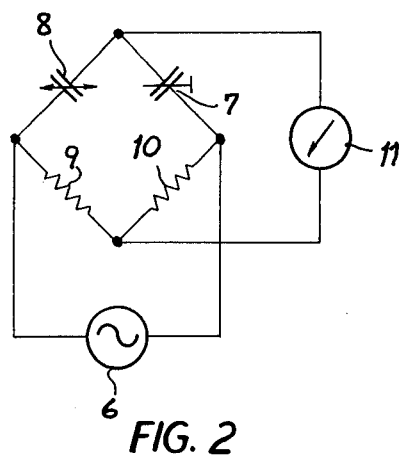
FIG. 2 is a circuit for the detector of FIG. 1.
Figure 3:
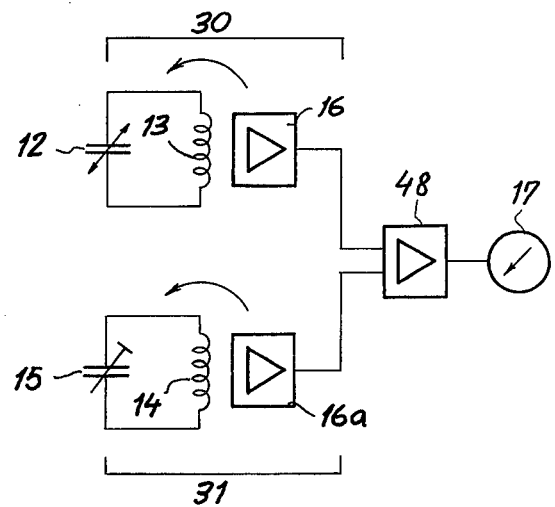
FIG. 3 is a circuit diagram, in block form, of another circuit for the detector of FIG. 1.

FIGS. 2 and 3 show electric circuits which can be used with the detector of the present invention. FIG. 2, for example, shows a capacitance bridge in which the energizing source 6 applies an alternating current across one of the diagonals of the bridge. The detecting capacitor is represented at 7 and is connected in one arm of the bridge while another arm of the bridge contains a reference capacitor 8, each arm being tied by a resistor 9 or 10 to an output terminal. The other output terminal of the bridge is the junction formed by the aforementioned arms. Across these terminals an indicator 11 is connected. The indicator 11 can, of course, be remote from the measuring site and can be simply a voltage measuring device. The output voltage across these terminals moreover, can be applied after rectification to a relay.

In FIG. 3, the detecting capacitor 12 forms part of a frequency control network, with the coil 13, of a diagrammatically shown oscillator whose output is applied by the amplifier transistor or other element 16 of this oscillator to a comparator 18. Similarly, a reference capacitor 15 in circuit with an inductor or coil 14 forms part of an oscillator circuit whose amplifier 16a feeds a characteristic frequency to the comparator or measuring stage 18. The oscillators represented generally at 30 and 31 are of the feed back type and are conventional in the art. When the two frequency control networks are at the same frequencies, corresponding to identical capacitances of the condenser 12 and 15, there is no output at the measuring stage 48 and hence no indication at 17 of the presence of liquid in the gas surrounding the detecting condenser 12.

When, however, the gas surrounding the condenser 12 contains liquid and the liquid is absorbed by the dielectric, the capacitance changes and the frequency of oscillator 31 shifts so that, at the measuring stage 48, an output is generated which is registered on the measuring or indicating device.

Figure 4:
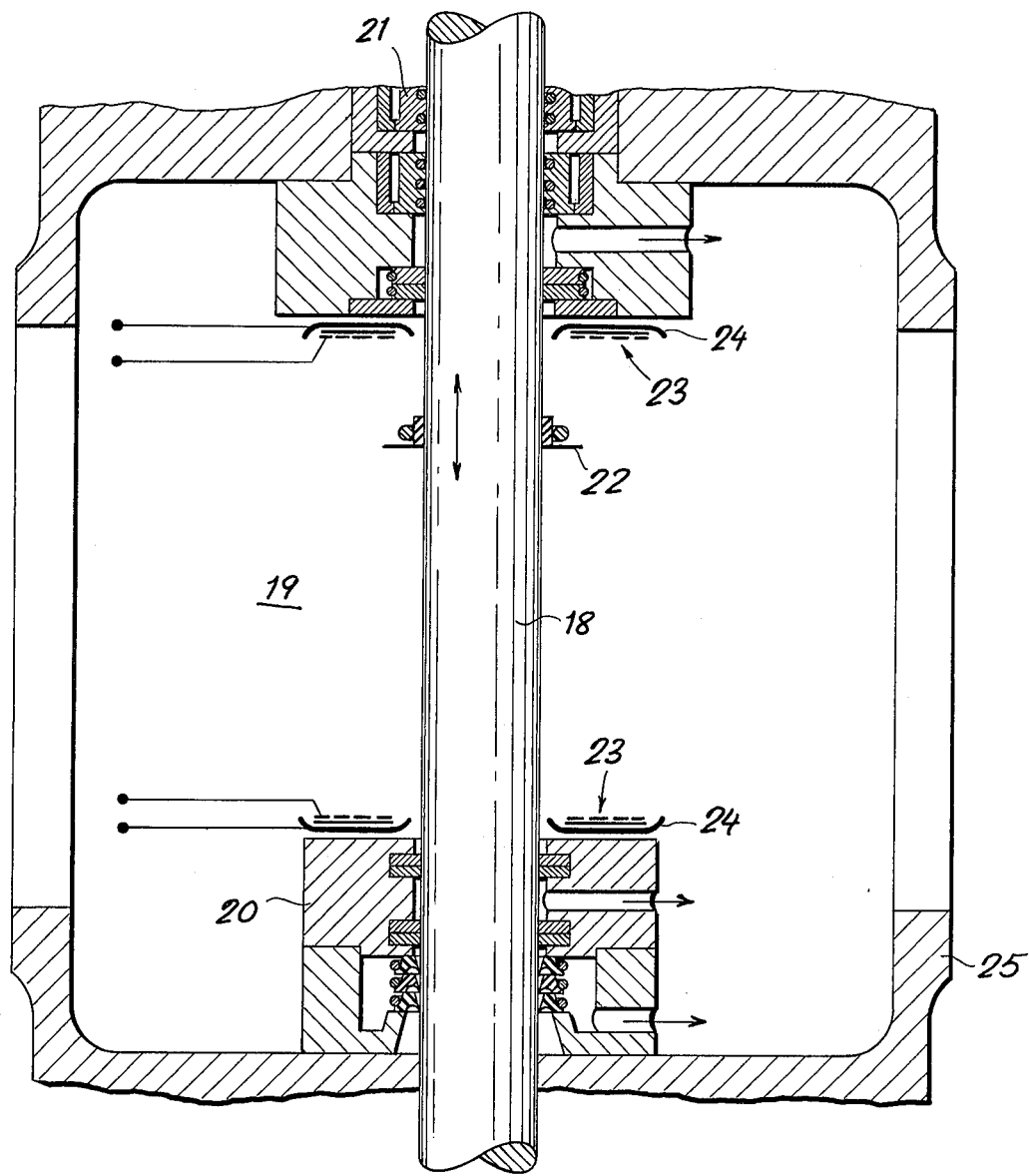
FIG. 4 is an axial cross-sectional view through the seal portions of a dry-running compressor showing the positions of a pair of detectors according to the invention.

FIG. 4 shows how the detector of the present invention is applied in a dry-running compressor. A dry-running compressor according to the invention thus has a housing 25 in which a piston rod 18 is reciprocatable in the direction of the double-headed arrow. The piston rod 18 is lubricated at its lower end and runs, at its upper end, dry. To prevent the penetration of oil into the space 19, the oil-stripping ring 20 is provided. In the dry-running section the piston rod 18 passes through the dry-running bushing 21. The piston rod 18 can have a ring 22 intended to prevent creeping of oil along its surface through the bushings 21.

According to an important feature of the invention, in the region of the dry-running bushing 21 and in the region of the oil-stripping ring 20 there are provided respective oil indicators 23 of the type described in FIGS. 1 through 3. Each of these indicators comprises an annular copper plate 24 with bent inner and outer peripheral edges which receive between them the ring of blotting paper and an annular piece of copper fabric to which one of the conductors is attached. The other conductor is, of course, attached to the copper plate 24. The copper plate 24 can lie directly against the dry-running bushing 21 and the oil-stripping ring 20 respectively. The detectors are connected to remote indicating devices (not shown in this FIGURE) to alert the operator to any penetration of oil into the dry-running space.

When oil from the oil-coated parts of the dry-running compressor is entrained with the piston rod 18 and is scattered into the gas space, it passes through the permeable parts of the oil detectors and is absorbed by the respective dielectric layers thereof. The resulting changes in dielectric constants are registered and measured (at 11 and 17) and preferably can operate an alarm circuit. The alarm circuit may have a visual or acoustic output. Especially in the case of dry-running compression of oxygen the alarm should turn off the compressor when the change of dielectric constant is detected.

Since the oil indicator can be remotely monitored, the dry-running compressor can be operated within fire-protective walls and is maintenance free. The incursion of oil is immediately detected so that corrective measures can be undertaken, e.g. from a central control station.

Figure 5:
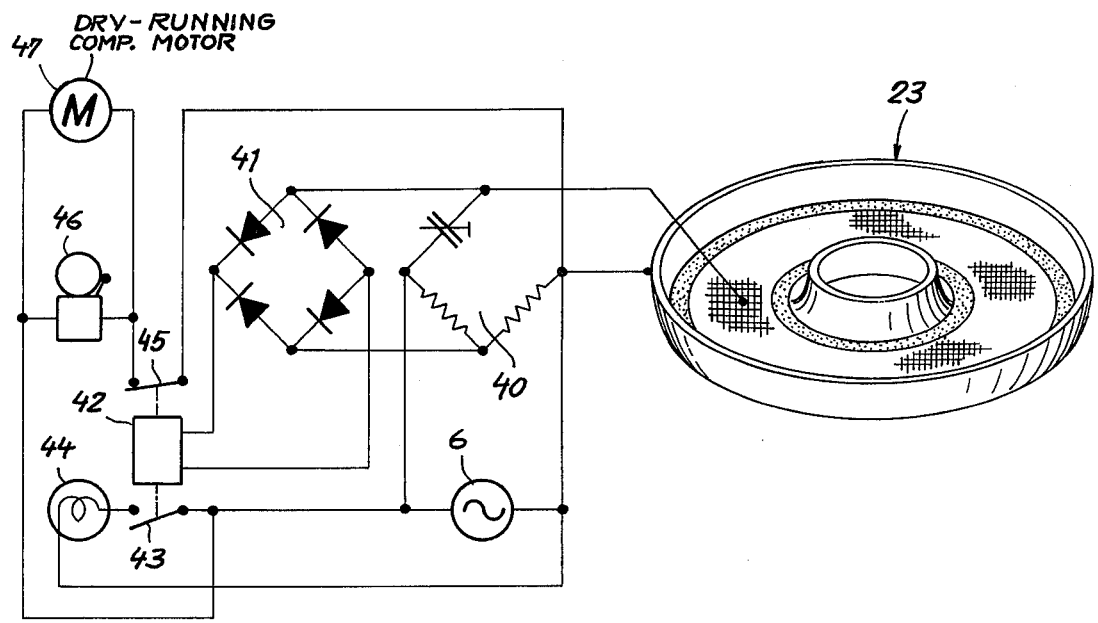
FIG. 5 is a diagram illustrating other circuitry for a detector according to the invention.

FIG. 5 shows, in somewhat greater detail, how the detector 23 can be connected into a capacitance bridge 40 of the type shown in FIG. 2, energized by an alternating current source 6. The output of the bridge is applied through a rectifier bridge 41 to a relay 42 having a normal open set of contacts 43 which operates the lamp 44 when lubricant is detected to alert the monitoring personnel. The relay 42 also has a set of contacts 45 which operate the acoustic alarm, e.g. bell 46, to terminate the ring thereof and alert personnel by the resulting silence and disconnect the drive motor 47 of the dry-running compressor.

We claim:

1. A dry-running compressor comprising:
   a housing forming a gas space;
   a linearly reciprocatable piston rod extending through said gas space;
   a dry-running bushing on said housing surrounding said piston rod at one side of said space;
   an oil stripping ring bushing surrounding said piston rod and received in said housing on an opposite side of said space; and
   respective oil detectors in said space adjacent each of said bushings for automatically indicating the incursion of oil into said base, each of said detectors comprising:
   a copper plate lying against the respective bushing;
   a layer of blotting paper disposed on the respective copper plate;
   a copper fabric disposed on the respective layer of blotting paper, said detectors each being annular and surrounding said piston rod; and
   respective circuit means connected across the plate and fabric of each detector and responsive to a change in capacitance thereof.

2. The dry-running compressor defined in claim 1 wherein said circuit means includes alarm means triggered upon a change in the capacitance of the respective layer of blotting paper.

3. The dry-running compressor defined in claim 2 wherein said circuit means includes a visual alarm.

4. The dry-running compressor defined in claim 2 wherein said alarm is an acoustic alarm.

5. The dry-running compressor defined in claim 2 wherein circuit means includes switch means whereby said compressor is turned off by a change in dielectric constant of said layer of blotting paper.

* * * * *